(12) United States Patent
Curry et al.

(10) Patent No.: US 7,286,224 B2
(45) Date of Patent: Oct. 23, 2007

(54) TIME-MULTIPLEXED SCANNING LIGHT SOURCE FOR MULTI-PROBE, MULTI-LASER FLUORESCENCE DETECTION SYSTEMS

(75) Inventors: Douglas N. Curry, Palo Alto, CA (US); Richard H. Bruce, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 193 days.

(21) Appl. No.: 11/018,759

(22) Filed: Dec. 21, 2004

(65) Prior Publication Data

US 2006/0132778 A1 Jun. 22, 2006

(51) Int. Cl.
G01N 21/64 (2006.01)
G01N 21/25 (2006.01)
G01J 3/24 (2006.01)
A61B 5/00 (2006.01)
G01N 21/76 (2006.01)

(52) U.S. Cl. ............... 356/318; 356/417; 422/82.08; 436/172; 600/317

(58) Field of Classification Search ........ 356/317–318, 356/417; 250/458.1–461.2; 422/82.07–82.08; 436/172; 600/317
See application file for complete search history.

(56) References Cited

U.S. PATENT DOCUMENTS

| | | |
|---|---|---|
| 4,002,829 A | 1/1977 | Hutchison |
| 4,010,364 A | 3/1977 | Fuwa |
| 4,556,903 A | 12/1985 | Blitchington et al. |
| 4,600,951 A | 7/1986 | Blitchington |
| 4,721,851 A | 1/1988 | Kogure |
| 4,849,645 A | 7/1989 | Mendenko et al. |
| 4,875,780 A | 10/1989 | Moran et al. |
| 4,941,309 A | 7/1990 | Fluent et al. |
| 5,017,798 A | 5/1991 | Murakami et al. |
| 5,216,485 A | 6/1993 | Bird et al. |
| 5,220,617 A | 6/1993 | Bird et al. |
| 5,315,993 A | 5/1994 | Alcala |

(Continued)

FOREIGN PATENT DOCUMENTS

GB 1 579 188 11/1980

(Continued)

OTHER PUBLICATIONS

Bianchi, Diana W., et al., Fetomatemal Cellular and Plasma DNA Trafficking, The Yin and the Yang, *Annals New York Academy of Sciences*, pp. 119-131.

(Continued)

*Primary Examiner*—Gregory J. Toatley, Jr.
*Assistant Examiner*—Bryan J Giglio
(74) *Attorney, Agent, or Firm*—Fay Sharpe LLP (57) ABSTRACT

An apparatus images a surface. An imager stage linearly translates the surface in a first direction. A light path has a first end defining an input aperture perpendicular to the first direction and parallel to the surface, and a second end defining an output aperture. A plurality of radiation beams linearly scan and interact in time-multiplexed alternating turns with the surface below the input aperture to produce a time-multiplexed light signal that is collected by the input aperture and transmitted by the light path to the output aperture. A photodetector arrangement detects the light signal at the output aperture. A processor processes the detected time-multiplexed light.

17 Claims, 7 Drawing Sheets

U.S. PATENT DOCUMENTS

| | | | |
|---|---|---|---|
| 5,471,066 A | 11/1995 | Hagiwara | |
| 5,627,365 A | 5/1997 | Chiba et al. | |
| 5,640,246 A | 6/1997 | Castonguay | |
| 5,651,047 A | 7/1997 | Moorman et al. | |
| 5,732,162 A | 3/1998 | Curry | |
| 5,798,831 A | 8/1998 | Hagiwara | |
| 5,892,577 A | 4/1999 | Gordon | |
| 6,445,451 B1 | 9/2002 | Douglas-Hamilton et al. | |
| 6,582,363 B2 | 6/2003 | Adachi et al. | |
| 6,636,623 B2 | 10/2003 | Nelson et al. | |
| 6,765,605 B1 * | 7/2004 | Inoue | 347/234 |
| 2001/0012386 A1 * | 8/2001 | Struye et al. | 382/131 |
| 2001/0046712 A1 | 11/2001 | Hang et al. | |
| 2002/0177885 A1 | 11/2002 | Eisfeld et al. | |
| 2002/0186368 A1 | 12/2002 | Rosengaus et al. | |
| 2003/0058440 A1 * | 3/2003 | Scott et al. | 356/318 |
| 2003/0152128 A1 | 8/2003 | Verhaegen | |
| 2004/0071330 A1 | 4/2004 | Curry | |
| 2004/0071332 A1 | 4/2004 | Curry | |
| 2004/0131241 A1 | 7/2004 | Curry et al. | |
| 2005/0046848 A1 * | 3/2005 | Cromwell et al. | 356/417 |

FOREIGN PATENT DOCUMENTS

| | | |
|---|---|---|
| JP | 4296642 | 10/1992 |
| JP | 6148085 | 5/1994 |
| JP | 9145631 A | 6/1997 |

OTHER PUBLICATIONS

Wolfe, Josh, A Thousand Dots of Light, *Forbes/Wolfe Nanotech Report*, May 29, 2002, www.Forbes.com.

Pertl, Barbara, MD, et al., Fetal DNA in Maternal Plasma: Emerging Clinical Applications, *The American College of Obstetricians and Gynecologists*, Published by Elsevier Science Inc., vol. 98, No. 3, Sep. 2001, pp. 483-490.

Bauer, Kenneth D., et al., Reliable and Sensitive Analysis of Occult Bone Marrow Metastases Using Automated Cellular Imaging, *Clinical Cancer Research*, vol. 6, pp. 3552-3559, Sep. 2000.

Witzig, Thomas E., et al., Detection of Circulating Cytokeratin-positive Cells in the Blood of Breast Cancer Patients Using Immunomagnetic Enrichment and Digital Microscopy, *Clinical Cancer Research*, vol. 8, 1085-1091, May 2002.

Ghossein, R.A., et al., Molecular Detection and Characterisation of Circulating Tumour Cells and Micrometastases in Solid Tumours, *European Journal of Cancer* 36 (2000) 1681-1694, Mar. 2000, Elsevier Science Ltd.

Flatmark, Kjersti, et al., Immunomagnetic Detection of Micrometastatic Cells in Bone Marrow of Colorectal Cancer Patients, *Clinical Cancer Research*, vol. 8, 444-449, Feb. 2002.

Méhes, Gábor, et al., Quantitative Analysis of Disseminated Tumor Cells in the Bone Marrow by Automated Fluorescence Image Analysis, *Cytometry (Communications in Clinical Cytometry)*, 42:357-362 (2000, Wiley-Liss, Inc.

Werther, M., et al., The Use of the CELLection Kit in the Isolation of Carcinoma Cells from Mononuclear Cell Suspensions, *Journal of Immunological Methods*, 238 (2000) 133-141, 2000 Elsevier Science B.V.

Burchill, SA, et al., Comparison of the RNA-Amplification Based Methods RT-PCR and NASBA for the Detection of Circulating Tumour Cells, *2002Cancer Research Campaign, British Journal of Cancer* (2002) 86, 102-109.

European Search Report, dated Jun. 2, 2006; EPC Application No. 05112370.1-2204.

European Search Report, completed Mar. 3, 2006; EPC Application No. 05112479.0-2204, Filed Dec. 20, 2005; Berlin.

* cited by examiner

TIME-MULTIPLEXED SCANNING LIGHT SOURCE FOR MULTI-PROBE, MULTI-LASER FLUORESCENCE DETECTION SYSTEMS

CROSS REFERENCE

The following co-pending application U.S. Ser. No. 10/616,366, Filed Jul. 9, 2003, is hereby incorporated by reference in its entirety.

BACKGROUND

The present exemplary embodiments relate to the imaging arts, and find particular application in conjunction with low and high-density cell detection, locating, and identifying in blood smears, biological assays, and the like across distinct imaging systems, and will be described with particular reference thereto. However, it is to be appreciated the exemplary embodiments will also find application in imaging, locating and identifying other types of low- or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

In rare cell studies, a particular problem arises due to the typically low concentration of the rare cells in the blood or other body fluid. In a typical rare cell study, blood is processed to remove cells that that are not needed. Then a fluorescent material is applied that attaches to antibodies, which in turn selectively attach to a cell surface or cellular protein of the rare cells. The cellular proteins may be membrane proteins or proteins within a cell, such as cytoplasm proteins. The antibodies may also attach to other types of molecules of the rare cell, as well as to DNA.

The fluorescent material may be a fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, for a one-in-one-million rare cell concentration. Such a blood smear typically occupies an area of about 100 $cm^2$. It is to be understood, however, that this is simply one example and other numbers of cells may be required for statistical accuracy for a particular test or study. Other cell identifiers which are being used and investigated are quantum dots and nano-particle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

In this regard, the ability to scan large numbers of cells at a high rate is considered a key aspect which increases the throughput of testing processes. Therefore, it is considered valuable to provide a system which improves the speed, reliability and processing costs which may be achieved by cell detection systems and/or processes.

A number of cell detection techniques have been proposed including fluorescence in situ hybridization (FISH), flow cytometry, laser scanning cytometry (LSC), among others. While the above-noted systems are directed to creating faster scan rates, they nevertheless still have relatively small fields of view (FOV), such as microscopes. This will, therefore, still result in speeds which do not reach the desired scan rates.

In view of this, the previously noted and incorporated U.S. application Ser. No. 10/271,347 discloses a fiber array scanning technology (FAST) that increases the speed at which scanning of a sample and the detection of potential or candidate rare cells may be accomplished, lending itself to the investigation of large samples. Still, while the aforementioned application provided an increased speed, a still further increase in speed can be accomplished by, e.g., providing a second laser that produces excitation light at a second wavelength or wavelength range and a second signal detector calibrated to sense a second fluorescence signal simultaneously with the first laser and signal detector. In this arrangement, each signal detector could be configured with a filter to sense only the desired respective fluorescence signal. This essentially doubles the amount of information that can be detected during a single scan.

One problem that arises with this arrangement, however, is that a portion of either stimulated fluorescence signal may significantly overlap the remaining fluorescence signal in terms of wavelength. Selective filtering can reduce this problem but at the cost of reducing the useful wavelength band that may be sensed. A second problem that arises is that this method would normally make use of a beam splitter or dichroic mirror in the light path of the fluorescent radiation in order to direct desired portions of the fluorescent signal to the respective signal detector, further reducing the intensity of the signal being sensed.

BRIEF DESCRIPTION

In accordance with one aspect of the present exemplary embodiments, an imager for imaging a sample is disclosed. An imager stage supports the sample. A light path has a proximate end defining an input aperture viewing the sample on the microscope stage. The light path further has a distal defining an output aperture disposed away from the imager stage. A plurality of scanning radiation sources is arranged in fixed relative positions to the input aperture. The scanning radiation sources each scan a radiation beam on the sample in alternating turns within a viewing area of the input aperture. Each radiation beam interacts with the sample to produce a light signal that is received by the input aperture and transmitted via the light path to the output aperture. Each scanning radiation source rasters the radiation beam over a selected area of the sample. A photodetector arrangement detects the light signal at the distal light path end, and a processor processes the detected light signals.

BRIEF DESCRIPTION OF THE DRAWINGS

The embodiments may take form in various components and arrangements of components, and in various steps and arrangements of steps. The drawings are only for purposes of illustrating preferred embodiments and are not to be construed as limiting the application.

DETAILED DESCRIPTION

Figure 1:
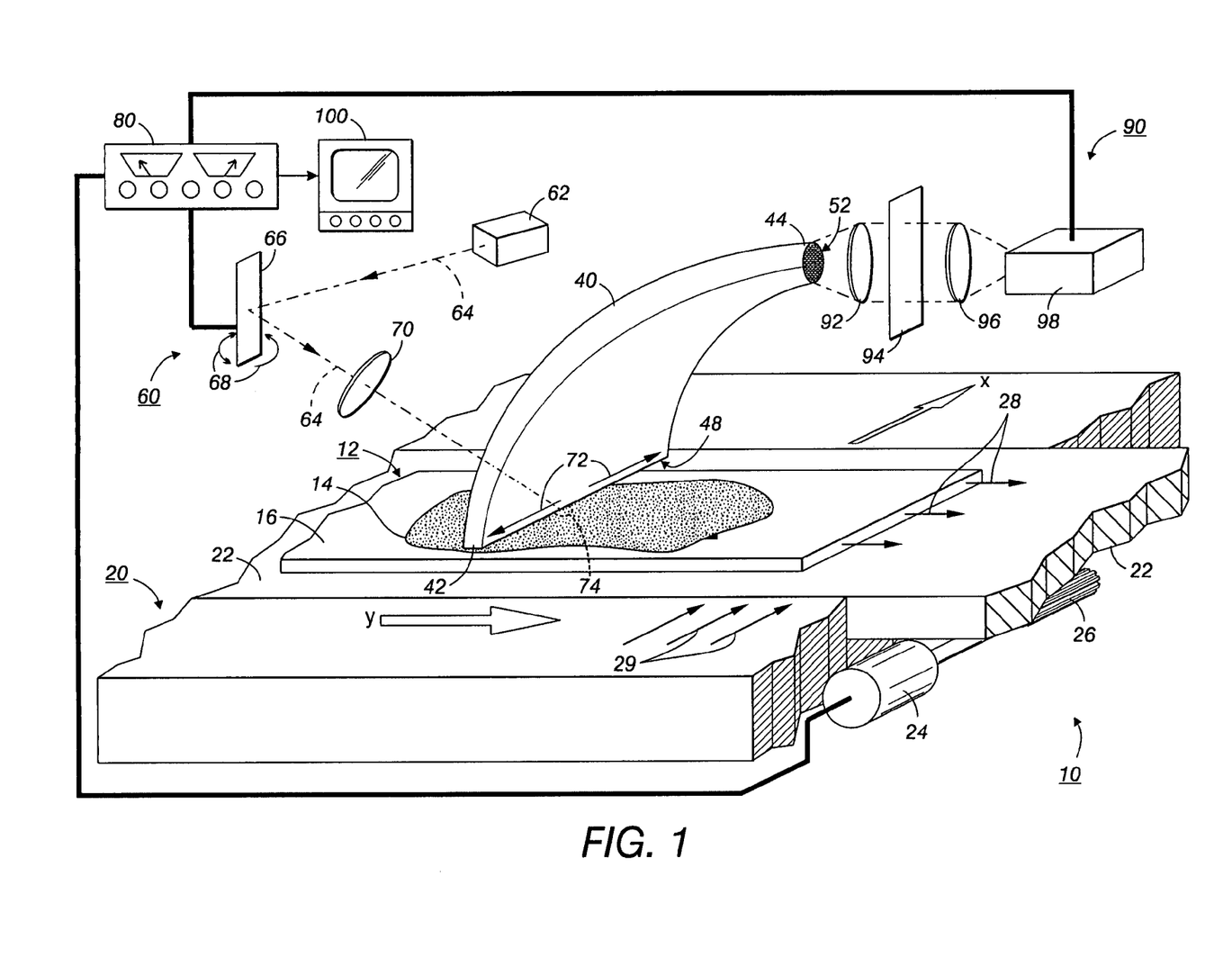
FIG. 1 shows a perspective view of an imaging apparatus suitable for incorporating features of a preferred embodiment.

With reference to FIG. 1, for purposes of understanding the embodiments described herein, an imaging apparatus is first described which utilizes a galvanometer-based laser scanning system with a single laser transmitter and a single detector. Various embodiments are then described which provide an increased scanning speed and which solve the aforementioned problems. In the figure, the imaging apparatus or imager 10 examines a sample 12 such as a biological smear 14 disposed on at least a portion of a surface of a slide 16. Imaging apparatus or imager 10, as expanded upon below, is designed for detection of minute or microscopic material.

As is known in the art, for cell studies the sample 12 is suitably prepared by drawing a sample of a biological fluid such as, but not limited to, blood or parts of blood from a subject. In a preferred embodiment, the sample is a monolayer of cells. The fluid sample is treated with a fluorescent material, such as but not limited to a marker dye that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Work is also being undertaken to develop marking materials for numerous other cells such as brain cells, liver cells, as well as bacteria cells, among others. The material preferably emits a characteristic output, such as a fluorescence or a phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths. While dyes are the predominant tagging process, other techniques exist including the use of markers known as quantum dots and DNA nano-particle probes.

The sample 12 is mounted on an imager translation stage, or slide holder, 20 (shown in part) which includes a linearly translatable track 22 that supports the sample 12. A motor 24 connects with the track 22 via gearing 26 to translate the track 22 and the supported sample 12 along a y-direction (indicated by arrows 28) and a x-direction (indicated by arrows 29). Although translation stage 20 driven by a rotary motor 24 is shown in FIG. 1, it is also contemplated to employ other types of mechanical driving devices. Furthermore, other types of sample movement such as sample rotation are also contemplated.

Figure 2:
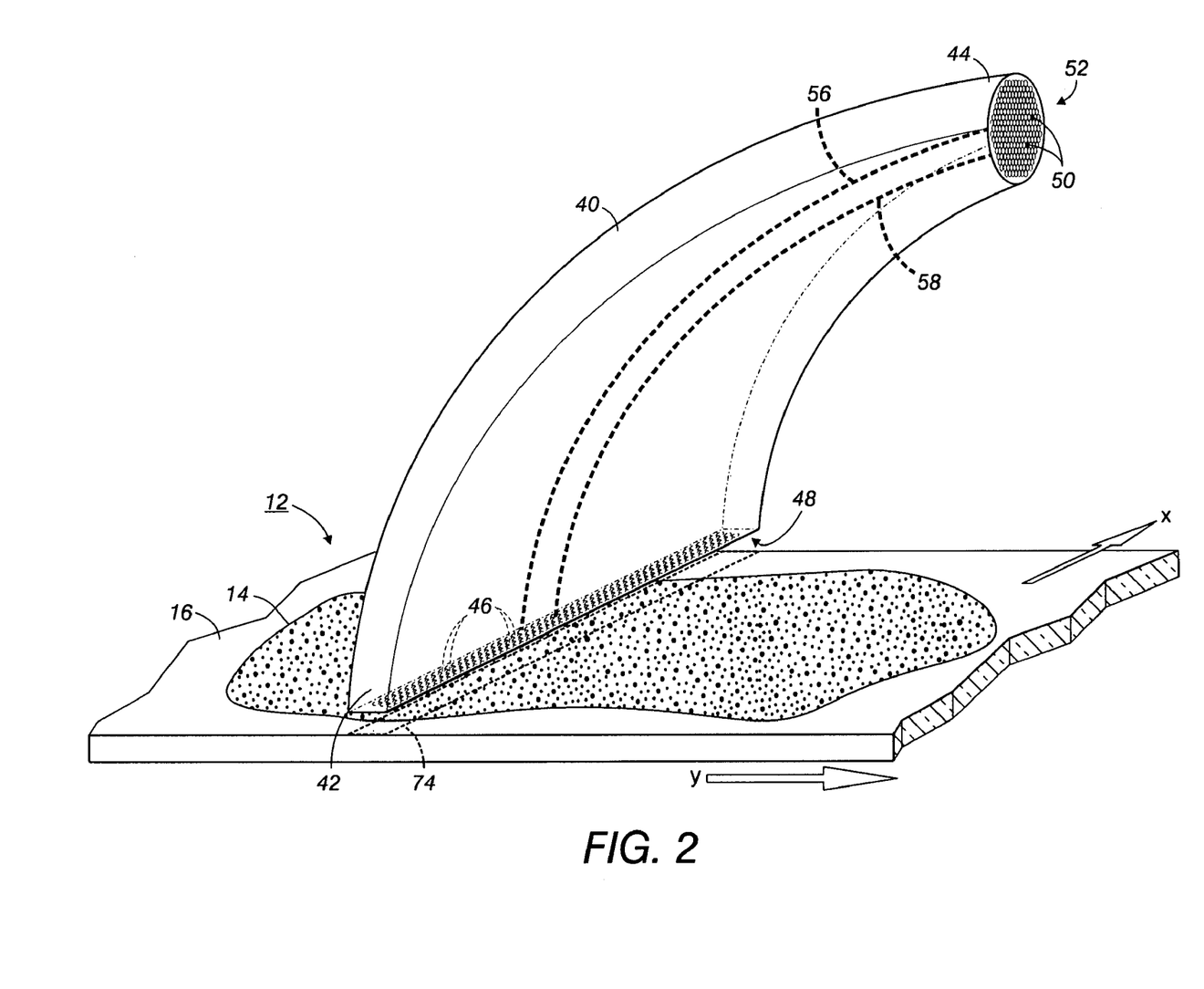
FIG. 2 shows an enlarged perspective view of the morphed fiber optic bundle of the imaging apparatus of FIG. 1 in relation to the sample.
Figure 3:
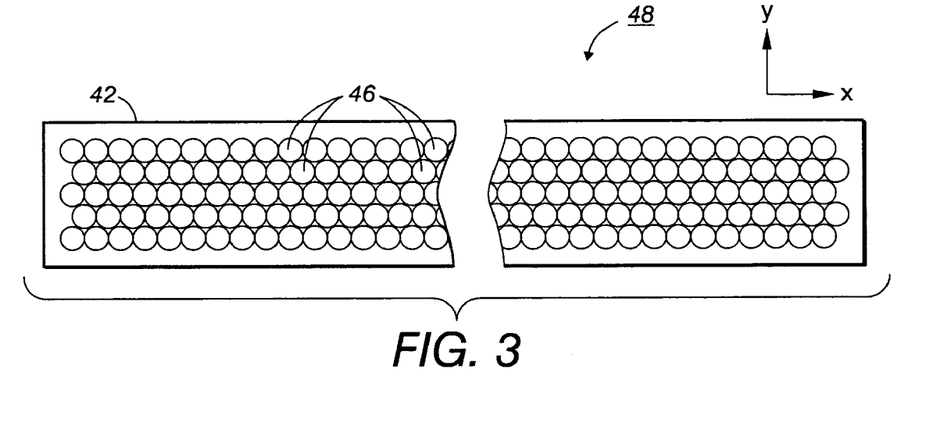
FIG. 3 shows an enlarged end view of the first end that defines the input aperture of the morphed fiber optic bundle of the apparatus of FIG. 1.

With continuing reference to FIG. 1 and with further reference to FIGS. 2 and 3, a fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 (best seen schematically in FIG. 3) with a long dimension aligned with the x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern, as shown in FIG. 3. Alternatively, the first fiber ends can be arranged in an irregular or non-periodic array and may have diameters which are greater or less than 50 microns. Although generally round fiber ends are shown, it is also contemplated to employ fibers with oval, square, hexagonal, or other cross-sectional shapes. The first fiber ends 46 are oriented substantially perpendicular to the plane of the biological smear 14 so as to view the smear 14.

The optical fiber bundle 40 "morphs" or changes cross-sectional dimensions and shape between the first end 42 to the second end 44 such that the second end 44 includes a plurality of second fiber ends 50 (best seen schematically in FIG. 2) that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. In FIG. 2, the paths of two exemplary individual, distinct fibers 56,58 are indicated as dotted lines. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

It is particularly pointed out that the spatial relationship between the first fiber ends 46 and the second fiber ends 50 is generally arbitrary. For example, in FIG. 2 the fibers 56, 58 run from approximately the same position in the input aperture 48. However, the fiber 56 terminates near a top of the output aperture 52, while the fiber 58 terminates near a middle of the output aperture 52. Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers 56, 58, and the overall length of the fibers 56, 58. Fiber bending losses are preferably reduced by avoiding sharp bends of the fiber optic bundle 40. For example, as seen in FIGS. 1 and 2, the difference in orientation of the input aperture 48 and the output aperture 52 is achieved by a gradual bend in the optical fiber bundle 40.

It is understood that while a fiber bundle has been described as the mode of transport of the acquired light, any other existing or subsequently developed light transmission component or light path or pipe which includes the appropriate characteristics may be employed as the light path or light pipe.

With continuing reference to FIGS. 1-3, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the galvanometer 66 translates into a linear sweeping or fast scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces-a spot size on the biological smear 14 which substantially comports with a size of the cells, which may vary in size but are typically about one to thirty microns in size. To obtain such narrow beam focusing, the focusing lens 70 is typically included.

With continuing reference to FIGS. 1-3, an electronic control unit 80 communicates with the galvanometer 66 and the translation stage 20 to coordinate the linear sweeping or scanning 72 of the radiation beam 64 along the trajectory 74 and the linear translation 28 of the sample 12 to effectuate a rastering of the radiation beam 64 across a selected area of the sample which is bounded in the x-direction by the smaller of a span of the trajectory 74 and the long dimension of the input aperture 42. Preferably, the span of the trajectory 74 substantially comports with the long dimension of the input aperture 42.

Excitation radiation beam 64 is incident upon the biological smear 14 at an oblique angle which is larger than a collection angle θ of the input aperture 42. The collection angle θ depends upon a short dimension of the input aperture 42, the distance between the input aperture 42 and the biological smear 14, and the light collecting characteristics of the first fiber ends 46. The latter is suitably characterized by a numerical aperture of the fiber ends. As is known in the art, an optical fiber end typically has a large numerical aperture corresponding to a large light collection angle which is particularly advantageous for collecting the typically weak characteristic luminescence of the cells. In a suitable embodiment, the radiation beam 64 impinges upon the sample 12 at 30°-90°. When beam 64 impinges upon sample 12 at approximately 90°, a bifurcated light path may be provided wherein light is collected on both sides of the scanning beam. One example of such-a bifurcated light path is shown in U.S. patent application Ser. No. 10/616,366, entitled Improved Method and Apparatus for Scanning and Light Collection for a Rare Cell Detector, hereby fully incorporated by reference.

Because the incidence angle of the radiation beam 64 is larger than the collection angle θ of the input aperture 42, specularly reflected radiation is not collected by the input aperture 42. However, the characteristic luminescence produced by the treated cells generally emits uniformly in all spatial directions, i.e. each treated cell corresponds to a point light source. Hence, a substantial portion of the characteristic luminescence is collected by the input aperture 42 due to its close proximity to and alignment with the radiation beam trajectory 74 on the biological smear 14 as well as the large numerical aperture of the first fiber ends 46. The collected light enters the first fiber ends 46, transmits along the individual fibers, e.g. the fibers 56, 58 shown in FIG. 2, and exits the optical fiber bundle 40 at second fiber ends 50 that correspond to the collecting first fiber ends 46.

It will be appreciated that the characteristic luminescence produced by a particular cell will not generally be collected by all or even most of the first fiber ends 46. Rather, only one or a few of the first fiber ends 46 which are closely proximate to the cell will collect the characteristic luminescence therefrom. In an exemplary embodiment, the radiation spot size is about 10-15 microns corresponding to a similarly sized cell, while each first fiber end 46 has a diameter of about 50 microns. Hence, only one or a few fibers may be needed to view and collect the characteristic luminescence for any given position of the sweeping radiation beam 64.

However, because at the second end 44 of the fiber bundle 40 the second fiber ends 50 are arranged to define the compact, output aperture 52, the characteristic luminescence emanates from a small region of space corresponding to the output aperture 52 regardless of which of the first fiber ends 46 collected the characteristic luminescence. As the excitation beam 64 sweeps along its trajectory 74 parallel to and typically below the input aperture 48, the proximate one or few of the first fiber ends 46 collect the characteristic luminescence, which is channeled by the fiber optic bundle 40 to the compact output aperture 52.

In one suitable embodiment, the blocking filter 94 is an interference filter with a reflectance peak coinciding with a center wavelength of the radiation beam 64 is employed. As is known in the art, optical interference filters have a rejection ratio that is strongly dependent upon the angle of incidence of the light. An exemplary interference filter used in one actually constructed embodiment exhibits a 106:1 or greater rejection ratio for light incident within ±14° of normal incidence. In this constructed embodiment, the first lens 92 includes a lens combination, designed using known optical design methods, that collimates light emanating from the output aperture 52 to within a ±10° angular divergence.

With continuing reference to FIG. 1, a second lens 96 focuses the collimated collected light onto a photodetector arrangement 98. By combining the compact output aperture 52 with focusing optics 92, 96, photodetector 98, which may be a single photodetector, provides signal detection for the spatially distributed linear input aperture 48. Because of the typically low collected characteristic luminescence intensities produced by treated cells, the photodetector 98 is preferably a photomultiplier tube. As is known in the art, a photomultiplier tube provides substantial signal gain through cascade multiplication of electrons in a multi-stage high-voltage cathode. To further improve the signal-to-noise ratio, the optical path of the signal detector 90 is preferably enclosed to substantially reduce noise due to stray light.

Those skilled in the art can suitably modify the signal detector 90 by addition, removal, or substitution of components to adapt it to specific imaging situations. For applications providing alternate signal-to-noise characteristics, a photodiode can be used for the photodetector 98. Similarly, the single photodetector 98 and multiple focusing elements 92, 96 can be replaced by a photodetector array having an area that comports with an area of the output aperture 52.

Figure 4:
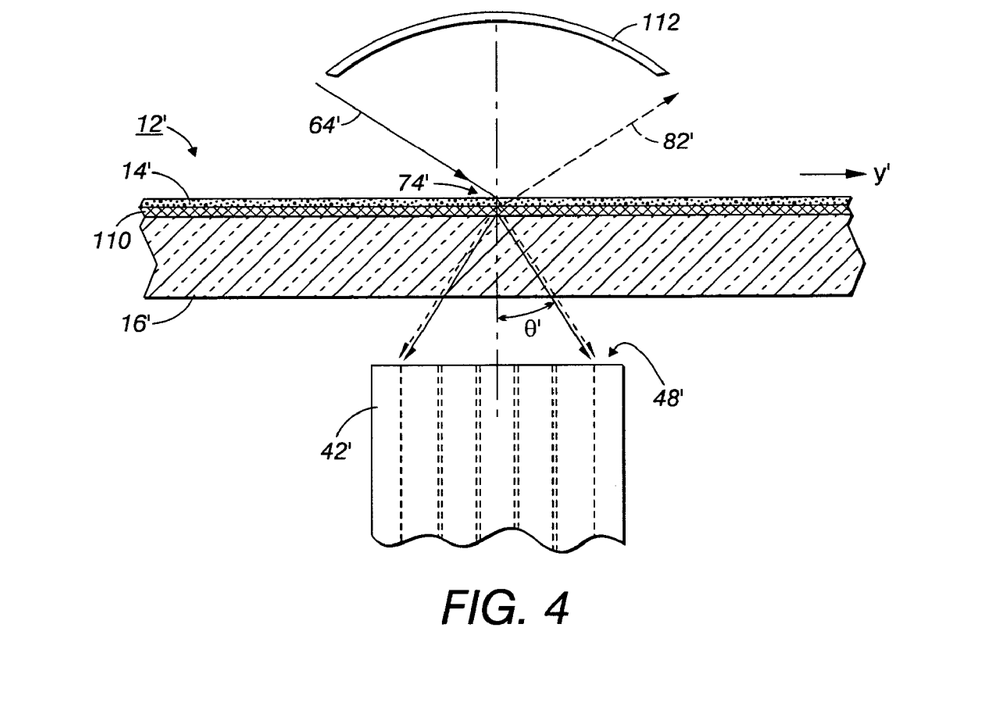
FIG. 4 shows a side view of another embodiment, the view centered on the first end of the morphed fiber optic bundle;.

Although the hereinbefore described embodiments show the stimulated emissions being collected by an aperture 48 arranged above the sample, it is to be appreciated that, as shown in FIG. 4 an input aperture 48' may be arranged to view the sample 12' from below, i.e., from a side of the slide 16' that is opposite the biological smear 14'. That is, the input aperture 48' views the biological smear 14' through the slide 16', which is light transmissive for the characteristic luminescence of the cells. The slide 16' may also include an optional laser blocking filter 110, such as an absorption band pass filter, coating the surface below the biological smear 14'. The embodiment of FIG. 4 may also include an optional cylindrical reflector 112 having a linear focal line generally coinciding with the radiation beam trajectory 74' on the biological smear 14'. The cylindrical reflector 112 can improve the signal to noise ratio for certain imaging applications by increasing the amount of characteristic luminescence that is collected. It will be recognized that the cylindrical reflector 112 can also be used in conjunction with the configuration of FIG. 1.

In the above-described embodiments, it would often be advantageous when scanning fluorescent probes decorating cells to use multiple probes, with each fluorescing at a different wavelength than the other. For example, multiple probes enable simultaneous measure of different cell properties. Multiple probes can also be used to identify and eliminate noise or artifacts. For efficient excitation, it is often desirable to excite each probe with a specific laser that is optimized for the probe's absorption range. It can also be desirable to measure emission from multiple probes excited by the same laser.

An application of multiple excitation sources is used in conjunction with dual-labeling of cells to eliminate probe aggregate artifacts. Here two probes are chosen to have sufficiently different emission wavelengths that the collective emission can be effectively separated by conventional emission filters. The problem inherent in this approach is that the longer wavelength emission is inefficiently stimulated by a single excitation laser and would be more efficiently excited by a laser whose wavelength is closer to its emission. To obtain proper ratios of the emissions from the dual probes with one excitation source, the long wavelength emitter is desirably present at a higher concentration in the mixture. Such high concentrations can cause a spread of the ratio of the emissions and can also cause aggregate formation. Since lower concentrations can be used with more efficient excitation, it can be valuable to excite each probe with a different laser source.

Figure 5:
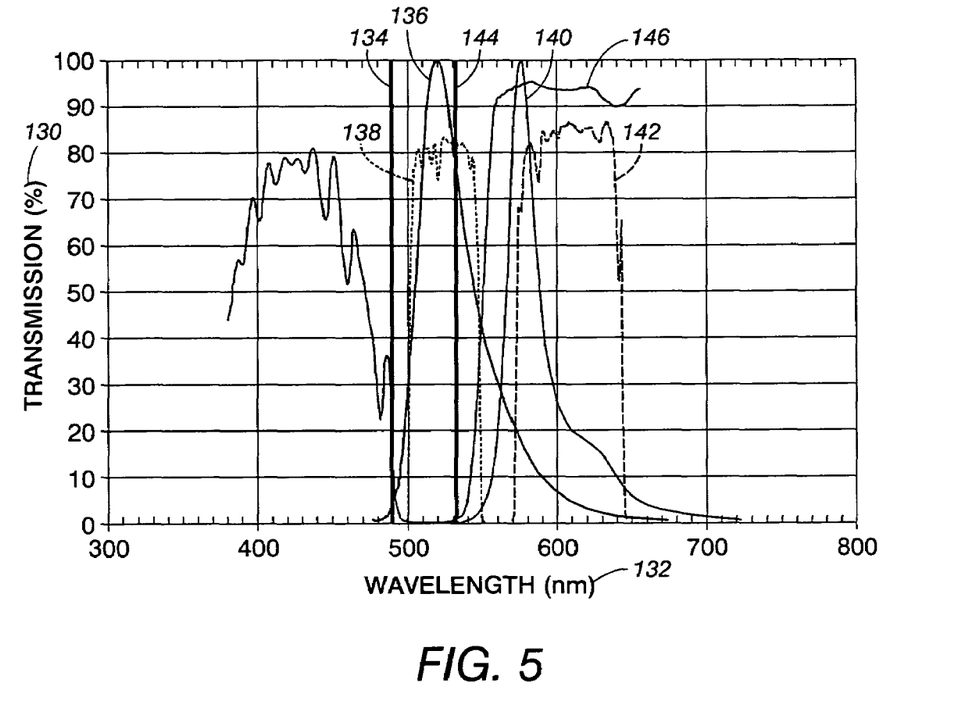
FIG. 5 shows a plot of excitation radiation and resultant stimulated radiation.

With reference to FIG. 5, the above-described problems associated with the use of dual probes, and dual laser sources, is shown. Transmission percentage 130 as a function of wavelength 132 is shown for exemplary wavelengths of interest. A first laser wavelength 134 is shown as a vertical line at 488 nm, which is a suitable laser wavelength for stimulating an FITC probe having a fluorescent emission 136 with peak emission intensity at approximately 520 nm. The difference in wavelength between the laser 134 and the peak emission wavelength of the FITC probe 136 is known in the art as the Stokes shift. Stokes shift is the difference in wavelength between absorbed and emitted quanta. The emitted wavelength is longer or equal to the incident wavelength due to energy conservation; the difference being absorbed as heat in the atomic lattice of the material. A first emission filter transmission curve 138 is shown which is suitable for filtering any undesirable reflections of the first laser, and other unwanted frequencies, while allowing substantial transmission of the desired probe fluorescence in the range of approximately 505 nm to 545 nm.

If a second R-PE probe 140 having a peak emission intensity at 576 nm is added simultaneously with the first probe 136, it may be observed that several problems arise. The emissions from the second probe overlap significantly with the emissions from the first probe (signal crosstalk) in the range of approximately 550 nm to 600 nm, making it difficult to differentiate between first and second probe emissions. In this exemplary case, a second emission filter 142 can be added with a transmission range from approximately 575 nm to 640 nm which partially alleviates the problem by blocking most of the first probe emissions. However, the same disadvantage still exists because of significant remaining crosstalk, even with the use of emission filters. For example, a significant portion of the first probe 136 emissions extends into the transmission band of the second emission filter 142 transmission curve, thereby reducing the sensitivity and signal-to-noise ration of the system.

The above-described signal loss is made more significant by the fact that only a single laser has been included in the system, and the second probe will not be stimulated as efficiently as the first probe because of the larger wavelength difference between the laser 134 and the second probe 140. To more efficiently stimulate the second probe, a second laser 144 emitting with a wavelength of 532 nm may be added, emitting simultaneously with the first laser 134. This, however, gives rise to another problem that is difficult to overcome. With a wavelength of 532 nm, the second laser falls within the transmission range of the first emission filter 138. Because of this, reflections of the second laser 144 may be erroneously detected as stimulated emissions from the first probe 136.

Figure 6:
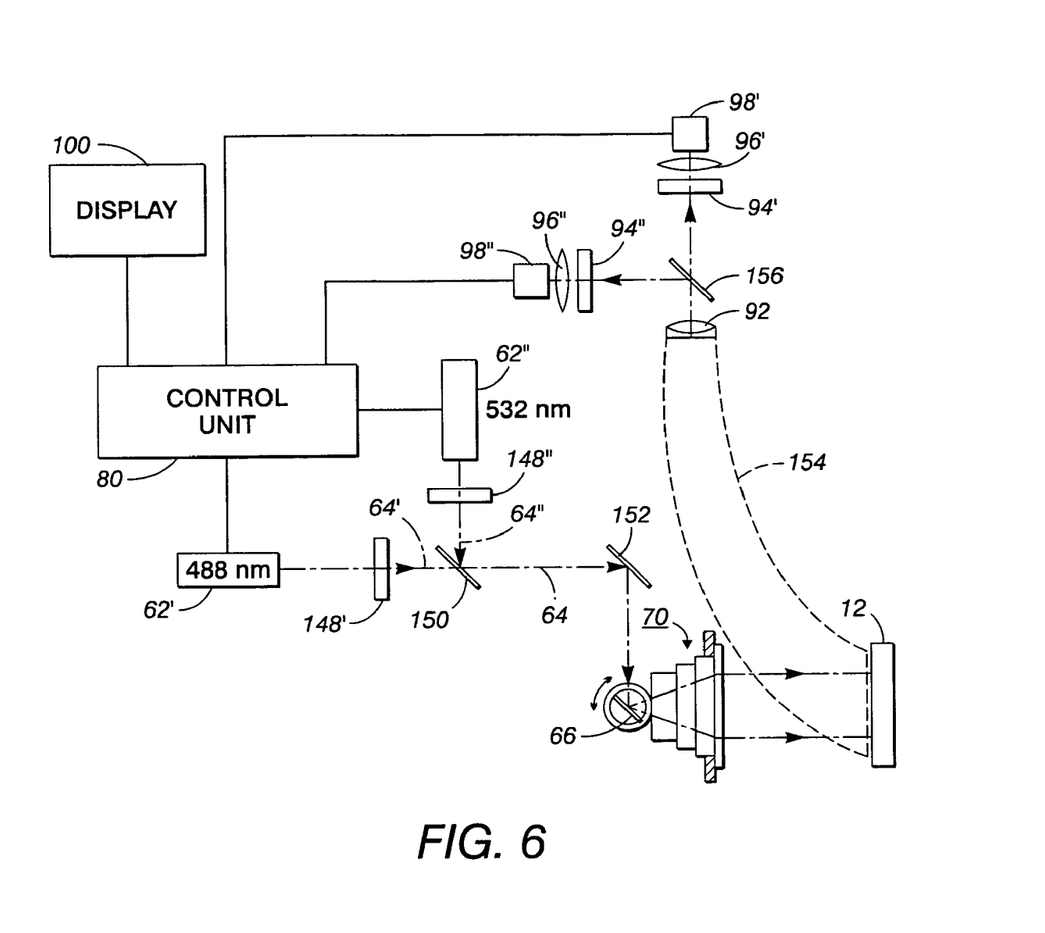
FIG. 6 shows a schematic view of features of a first embodiment.

With continuing reference to FIG. 5, and further reference to FIG. 6, shown schematically is an embodiment providing two or more signal detectors, and two or more lasers, which solves the aforementioned problems that arise when using dual probes (or multiple probes), by time-multiplexing the lasers. In this embodiment, the sample is stimulated sequentially, rather than simultaneously, with different laser wavelengths so there is no overlap of the probe's emission spectra by an excitation source. And also, signal crosstalk is reduced because the laser stimulating the first probe is only poorly stimulating the second probe which causes the crosstalk. To illustrate further, without time-multiplexing the lasers, a dichroic mirror having a transmission curve 146 would typically be used to separate the first and second probe emissions 136 and 140. It may be observed in FIG. 5 that a significant portion of the first probe emissions 136 fall undesirably within the transmission region of the dichroic mirror transmission curve 146, i.e., for wavelengths greater than approximately 520 nm.

The embodiment shown in FIG. 6 is shown in simplified form in order to facilitate an understanding of the described embodiments. A first dichroic mirror 150 receives light 64' from a first laser 62' and light 64" from a second laser 62" operating at, e.g., 488 nm and 532 nm respectively. The received lights are selectively provided as beam 64. The excitation signal from each laser is first passed through respective shutters 148' and 148". The shutters are coordinated so the single beam 64, at any given time, only contains light from one of the laser sources. Beam 64 is reflected by a reflective device 152 to the galvanometer 66 which scans the reflected beam through the optional lens arrangement 70 to the sample 12, generally operating as described previously with reference to FIG. 1.

Stimulated fluorescence from first and second probes in the sample 12 is received and transmitted along a light path 154 to the first lens 92. The focused light beam in light path 154 is then appropriately split by a second dichroic mirror 156, and selective portions of the light beam of the light path 154 are received by the respective photodetectors 98' and 98". Each of the photodetectors may be preceded in the light path by respective blocking filters 94' and 94", and second lens arrangements 98' and 98". In this manner, each of the photodetectors 98' and 98" can detect the fluorescence from the respective probes, and communicate the detected intensity levels to the control unit 80. Alternately, a single photodetector may be utilized by replacing the shown blocking filter arrangement with, e.g., a rotating disk having blocking filters 94' and 94" mounted in the disk, wherein the rotation of the disk is synchronized with the laser shutters 148' and 148".

Figure 7:
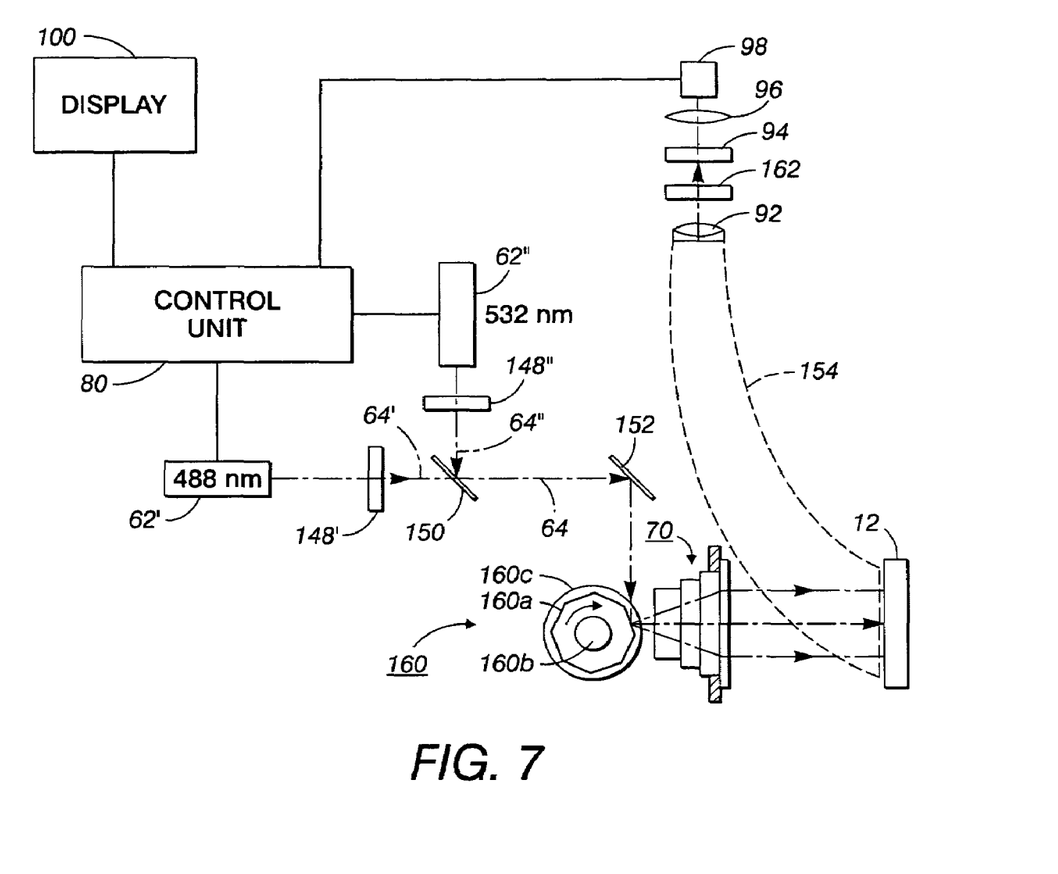
FIG. 7 shows a schematic view of features of an alternate embodiment.

FIG. 7 shows an alternative embodiment which addresses the aforementioned issues, providing the benefits of a reduced total scanning time. In this embodiment, the sample is also stimulated sequentially, rather than simultaneously. This is accomplished by using a rotating polygon scanner arrangement 160, shown in this exemplary system as a multi-sided mirror 160a, rotated by a motor 160b, and with a flywheel 160c, where the motor and flywheel permit for smooth rotation which eliminates signal jitter. As shown, the scanner arrangement scans a laser beam across the sample surface. In this particular embodiment, one side of the polygon mirror 160 scans the beam from the first laser 62' while another mirror of the polygon scanner scans the beam from laser 62". This device enables the method of sensing emission by all probes from each laser with no laser interference. For example with dual probes as shown, it can be valuable to sense the emission from both probes excited by a first laser while also sensing the emission of a specific probe excited by a second laser. In the embodiment shown in FIG. 7, only one photodetector 98 has been shown, and time multiplexed filtering, if necessary, is accomplished by filter 162. It is to be appreciated, however, that embodiments utilizing multiple photodetectors are intended to fall within the scope of this disclosure, and the use of the time-multiplexed filter 162 is optional.

Figure 8:
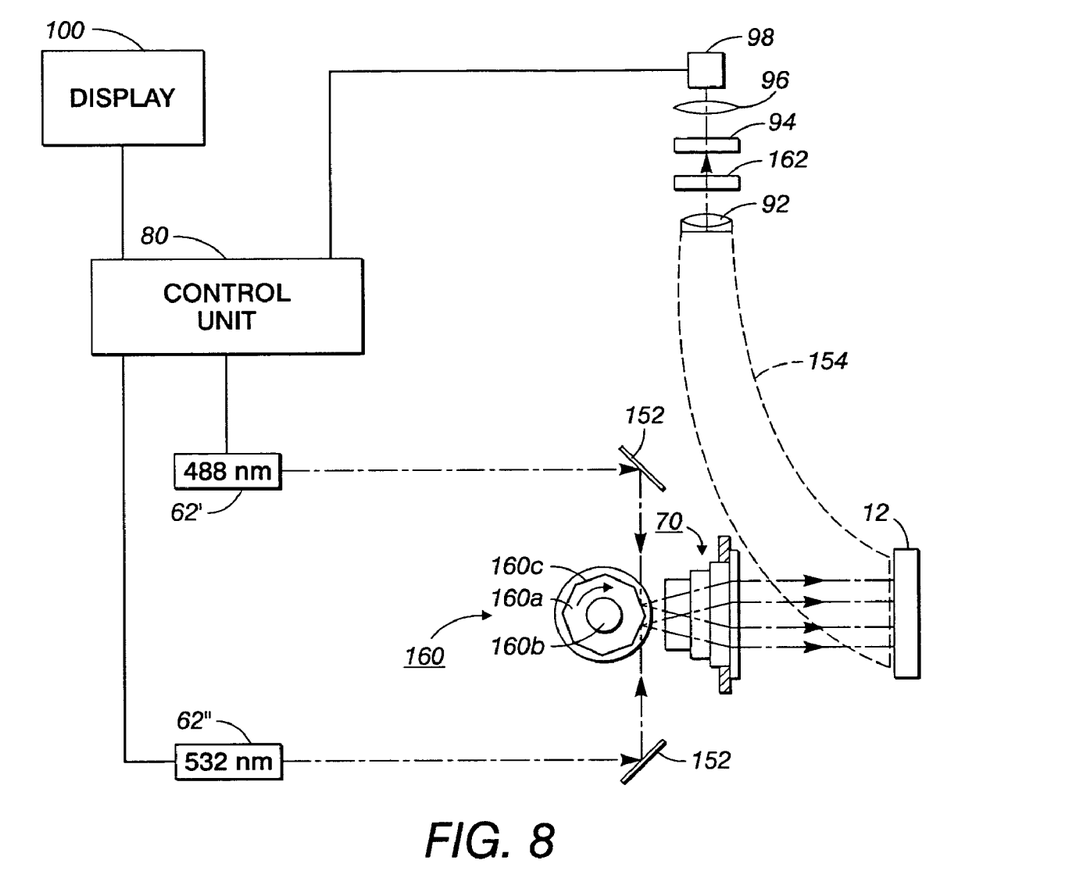
FIG. 8 shows a schematic view of features of a further embodiment.

FIG. 8 shows a further embodiment which also addresses the aforementioned issues. In this embodiment, the sample is also stimulated sequentially, rather than simultaneously. This embodiment also uses a polygon scanner arrangement which scans the laser beam across the sample surface, however, in this embodiment, an additional scan is,automatically inserted for each laser between scans provided by the embodiment of FIG. 7, thereby doubling the scan rate without increasing the speed of the polygon mirror 160. By proper placement of the angles of incidence from the lasers, the polygon automatically accomplishes the sequential scanning, including the additional inserted scans, without the use of shutters at each of the lasers. In the example shown, because of the placement of the lasers 62' and 62" each side of the polygon scanner arrangement 160 first scans the beam from the first laser 62' and then sequentially scans the beam from the second laser 62" for the direction of rotation shown. The additional scan for each side of the mirror effectively doubles the number of scans. It is to be noted that the concept may be extended to any number of appropriately positioned lasers. The polygon scanner may also have any desired number of sides.

The embodiment shown in FIG. 8 works particularly well if the scanning efficiency is less than 50%, thereby allowing room for the automatically inserted scan. An advantage of this system and method is that an extra scan is inserted without increasing the polygon rotation rate or lowering the overall process speed. An additional advantages lies in the fact that the rotating scanner arrangement 160 produces less jitter that the oscillating galvanometer used in a previously described embodiment. Still further, the embodiment shown in FIG. 8 can potentially double the amount of information detected in a single scan, thereby reducing total scanning time significantly. It is to be appreciated that the arrangement and order of components provided in the figure represent an exemplary embodiment only, and the present disclosure is not limited by the arrangement of components.

With any of the embodiments shown in FIGS. 6-8, the degradation of fluorescence signal due to an overlapping laser frequency is essentially eliminated. Further, signal crosstalk is reduced because the desired probe can be stimulated with a laser frequency that maximizes its emission, while adjacent crosstalk-producing probes are stimulated at inefficient emission frequencies. Each of these solutions significantly lowers the cost of the filtering system while upgrading its performance in a multi-probe, multi-laser fluorescence system. The embodiment shown in FIG. 8 can double the number of scans provided by the embodiment shown in FIG. 7, without increasing the speed of rotation of the polygon mirror or the scan rate.

Another aspect of the time-multiplexed scanning as described in the embodiments lies in the fact that autofluorescence noise is higher near the excitation wavelength and diminishes for stimulated emission wavelengths farther from the excitation wavelength. As was shown with reference to FIG. 5, the first emission filter transmission curve 138 was necessarily configured to block a significant portion of the longer wavelengths of the FITC fluorescent emission 136 in order to filter out the crosstalk with the simultaneous R-PE fluorescent emission 140. Because the crosstalk is essentially eliminated by time-multiplexed scanning, it is no longer necessary to block the longer wavelength emissions of a particular probe, thereby improving the signal-to-noise ratio which is valuable in certain image filtering operations.

Although the embodiments have been described with particular reference to cell identification, the described concepts are not limited in application thereto. The imager apparatus configurations shown in FIGS. 6-8 are suitable for many imaging applications in which features are to be identified or located. In one such application lying in the biomedical arts, typically ten to ten thousand DNA elements are arranged in an array known in the art as a DNA chip. The DNA elements are processed so that selected elements include a fluorescent tag. The embodiments shown are suitable for identifying the tagged DNA elements in a DNA chip that includes a large number of DNA elements. Implementing the concepts described in the foregoing permits for an imaging apparatus that can access the sample several times faster than existing technology.

The application has been described with reference to the preferred embodiments. Obviously, modifications and alterations will occur to others upon reading and understanding the preceding detailed description. It is intended that the disclosure be construed as including all such modifications and alterations insofar as they come within the scope of the appended claims or the equivalents thereof.

The invention claimed is:

1. A scanning imager for imaging a sample, the imager including:
   an imager stage that supports the sample;
   a light path having a proximate input aperture viewing the sample on the imager stage and a distal output aperture
   a plurality of scanning radiation sources, each arranged in a fixed relative position to the input aperture, groups of one or more of the scanning radiation sources, in alternating turns with the remaining scanning radiation sources, scanning a radiation beam on the sample within a viewing area of the input aperture, the radiation beam interacting with the sample to produce light signals that are received by the input aperture and transmitted via the light path to the output aperture;
   a rotating polygon scanner having two or more reflective surfaces, wherein the plurality of radiation sources is arranged so that each reflective surface scans, in alternating turn, radiation from at least two of the scanning radiation sources over a selected area of the sample, thereby increasing the number of scans for each revolution of the rotating polygon scanner;
   a photodetector system arranged to detect the light signals received from the output aperture respective to each group of the scanning radiation sources; and
   a processor that processes the light signal detected by the photodetector respective to each group of the scanning radiation sources.

2. The imager as set forth in claim 1, wherein the light signals are generated from fluorescent probes fluorescing at different wavelengths.

3. The imager as set forth in claim 2, wherein the light signals of the fluorescent probes received by the photodetector system are non-interfering light signals such that one light signal does not interfere with other light signals.

4. The imager as set forth in claim 1, further including:
   a plurality of shutters arranged to admit radiation from each of the radiation sources in alternating turn.

5. The imager as set forth in claim 1, further including:
   a motor arranged to move the sample in one of a translational and a rotational motion, the motor cooperating with the plurality of scanning radiation sources to effectuate a rastering of the radiation beam over a selected area of the sample.

6. The imager as set forth in claim 5, wherein the input aperture has a generally linear shape, the plurality of scanning radiation sources scans the radiation beam along a beam trajectory parallel to the generally linear aperture, and the motor linearly translates the sample along a trajectory that is perpendicular to the beam trajectory.

7. The imager as set forth in claim 5, wherein the motor rotates the sample about an axis that is normal to a surface of the sample, the input aperture has a generally linear shape extending radially away from the rotational axis, and the plurality of scanning radiation sources scans the radiation beam along a beam trajectory parallel to the generally linear aperture.

8. The imager as set forth in claim 1, including:
   a photodetector system coupled to the output aperture for detecting the emitted light signal.

9. The imager as set forth in claim 8, wherein the photodetector system includes a plurality of photodetectors, each photodetector configured to receive and detect the emitted light signal corresponding to one or more of the plurality of scanning radiation sources.

10. The imager as set forth in claim 9, further including:
    at least one lens for focusing the light signal from the output aperture onto at least one of the photodetectors.

11. The imager as set forth in claim 9, wherein the photodetector system includes at least one photomultiplier tube serving as a photodetector.

12. The imager as set forth in claim 9, wherein at least one of the plurality of scanning radiation sources is a light scanner, the imager further including:
    a light filter arranged to substantially block light produced by the light scanner from reaching the photodetector.

13. A scanning imager for imaging a generally planar surface, the imager including:
    a linearly translating stage that linearly translates the surface in a first direction;
    a light path arranged to define a linear input aperture disposed perpendicular to the first direction and parallel to the surface, and a second end defining a generally circular output aperture;
    a plurality of scanning radiation sources, wherein groups comprising one or more of the scanning radiation sources, in time-multiplexed turn with the remaining scanning radiation sources, linearly scan a radiation beam along the generally planar surface below the input aperture, the radiation beam interacting with the surface to produce a light signal that is collected by the input aperture and transmitted by the light path to the output aperture;
    a polygon scanner having at least two reflective surfaces, arranged to cooperate with the plurality of scanning radiation sources, wherein each of the reflective surfaces scans the radiation beam from each of the groups of radiation sources in alternating turns;
    a photodetector system arranged detect the light signal at the generally circular output aperture respective to each group of the scanning radiation sources; and
    a rastering processor communicating with the imager stage and the plurality of scanning radiation sources to coordinate the scanning of the radiation beam and the linear translation of the surface to effectuate a rastering of the radiation beam on the surface.

14. The imager as set forth in claim 13, wherein the light path includes a fiber optic bundle having a first end of parallel first fiber ends arranged to define the linear input aperture, and a second end defining the output aperture, wherein each first fiber end optically communicates with the generally circular output aperture.

15. An imaging method comprising:
    alternatingly reflecting radiation from a plurality of radiation beams off at least two surfaces of a rotating polygon scanner, thereby increasing the number of scans for each revolution of the rotating polygon scanner;
    sweeping each of the plurality of reflected radiation beams, each having varying radiation wavelengths along a linear path on a sample in time-multiplexed turns;
    collecting light produced by beam interaction of each of the radiation beams with the sample;
    transmitting the collected light along a light path, the light path channeling the collected light to a selected output region;

detecting the collected light of each beam interaction at the selected output region respective to each radiation beam;

moving the sample generally perpendicularly to the linear path of the plurality of radiation beams sweeping, the moving cooperating with the sweeping to raster the time-multiplexed radiation beams on the sample; and coordinating the sweeping, moving, and detecting to generate an array of picture elements representative of at least a portion of the sample for each of the beam interactions.

16. The imaging method as set forth in claim 15, wherein the collected light is from at least two probes having distinct emission wavelengths.

17. A scanning imager far imaging a sample, the imager including:

an imager stage that supports the sample;

a light path having a proximate input aperture viewing the sample on the imager stage and a distal output aperture;

a plurality of scanning radiation sources, each arranged in a fixed relative position to the input aperture, groups of one or more of the scanning radiation sources, in alternating turns with the remaining scanning radiation sources, scanning a radiation beam on the sample within a viewing area of the input aperture, the radiation beam interacting with the sample to produce light signals that are received by the input aperture and transmitted via the light path to the output aperture;

a rotating polygon scanner having two or more reflective surfaces, wherein the plurality of radiation sources is arranged so that each reflective surface scans, in alternating turn, radiation from at least two of the scanning radiation sources over a selected area of the sample, thereby increasing the number of scans for each revolution of the rotating polygon scanner;

wherein a motor rotates the sample about an axis that is normal to a surface of the sample, the input aperture has a generally linear shape extending radially away from the rotational axis, and the plurality of scanning radiation sources scans the radiation beam along a beam trajectory parallel to the generally linear aperture;

a photodetector system arranged to detect the light signals received from the output aperture respective to each group of the scanning radiation sources; and a processor that processes the light signal detected by the photodetector respective to each group of the scanning radiation sources.

* * * * *